(12) United States Patent
Lui et al.

(10) Patent No.: US 10,213,607 B2
(45) Date of Patent: *Feb. 26, 2019

(54) USER INTERFACE WITH VIEW FINDER FOR LOCALIZING ANATOMICAL REGION

(71) Applicant: Boston Scientific Neuromodulation Corporation, Valencia, CA (US)

(72) Inventors: Mun Pook Lui, Northridge, CA (US); Sridhar Kothandaraman, Valencia, CA (US); Gyuman Kim, Lynnwood, WA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 58 days.

This patent is subject to a terminal disclaimer.

(21) Appl. No.: 15/254,422

(22) Filed: Sep. 1, 2016

(65) Prior Publication Data

US 2016/0367828 A1    Dec. 22, 2016

Related U.S. Application Data

(63) Continuation of application No. 13/445,179, filed on Apr. 12, 2012, now Pat. No. 9,433,795.

(Continued)

(51) Int. Cl.
*A61N 1/05* (2006.01)
*A61N 1/372* (2006.01)
*A61N 1/36* (2006.01)

(52) U.S. Cl.
CPC ........ *A61N 1/37247* (2013.01); *A61N 1/0551* (2013.01); *A61N 1/36071* (2013.01)

(58) Field of Classification Search
CPC . A61N 1/372; A61N 1/37235; A61N 1/37247
See application file for complete search history.

(56) References Cited

U.S. PATENT DOCUMENTS

| 6,516,227 B1 | 2/2003 | Meadows et al. |
| 6,895,280 B2 | 5/2005 | Meadows et al. |

(Continued)

FOREIGN PATENT DOCUMENTS

| JP | 2005502936 A | 1/2005 |
| JP | 2005100279 A | 4/2005 |

(Continued)

OTHER PUBLICATIONS

"U.S. Appl. No. 13/445,179, Advisory Action dated Aug. 4, 2014", 4 pgs.

(Continued)

*Primary Examiner* — Joseph M Dietrich
(74) *Attorney, Agent, or Firm* — Schwegman Lundberg & Woessner, P.A.

(57) ABSTRACT

An external control device for use with a medical component implanted within a patient. The device comprises a user interface configured for receiving user input, displaying a first graphical representation of the medical component in the context of a global graphical representation of an anatomical region of the patient, displaying a view finder defining a portion of the global graphical representation, and displaying a second graphical representation of the medical component in the context of a local graphical representation of the portion of the anatomical region portion. The external control device further comprises control circuitry configured for, in response to the input from the user, modifying the displayed view finder to spatially define a different portion of the global graphical representation, such that the second graphical representation of the medical component is displayed in the context of a local graphical representation of the different portion of the anatomical region.

20 Claims, 9 Drawing Sheets

Related U.S. Application Data

(60) Provisional application No. 61/474,884, filed on Apr. 13, 2011.

(56) References Cited

U.S. PATENT DOCUMENTS

| | | | |
|---|---|---|---|
| 6,993,384 | B2 | 1/2006 | Bradley et al. |
| 7,392,076 | B2 | 6/2008 | Moctezuma De La Barrera |
| 7,423,660 | B2 | 9/2008 | Ouchi et al. |
| 7,555,725 | B2 | 6/2009 | Abramson et al. |
| 7,848,802 | B2 | 12/2010 | Goetz et al. |
| 8,233,992 | B2 | 7/2012 | Zhu et al. |
| 8,380,301 | B2 | 2/2013 | Zhu |
| 9,433,795 | B2 | 9/2016 | Lui et al. |
| 2007/0203538 | A1 | 8/2007 | Stone et al. |
| 2007/0203545 | A1 | 8/2007 | Stone et al. |
| 2008/0154340 | A1 | 6/2008 | Goetz et al. |
| 2008/0215119 | A1 | 9/2008 | Woods et al. |
| 2010/0010566 | A1 | 1/2010 | Thacker et al. |
| 2010/0121409 | A1 | 5/2010 | Kothandaraman et al. |
| 2010/0137944 | A1 | 6/2010 | Zhu |
| 2011/0054551 | A1 | 3/2011 | Zhu et al. |
| 2012/0265269 | A1 | 10/2012 | Lui et al. |

FOREIGN PATENT DOCUMENTS

| | | | |
|---|---|---|---|
| JP | 2005137904 A | | 6/2005 |
| JP | 2014517738 A | | 7/2014 |
| JP | 6108629 B2 | | 3/2017 |
| WO | WO-2008070140 A2 | | 6/2008 |
| WO | WO-2009134478 A1 | | 11/2009 |

OTHER PUBLICATIONS

"U.S. Appl. No. 13/445,179, Appeal Brief filed Sep. 17, 2014", 16 pgs.

"U.S. Appl. No. 13/445,179, Examiner Interview Summary dated Dec. 31, 2015", 3 pgs.

"U.S. Appl. No. 13/445,179, Final Office Action dated May 21, 2014", 7 pgs.

"U.S. Appl. No. 13/445,179, Final Office Action dated Jul. 12, 2013", 5 pgs.

"U.S. Appl. No. 13/445,179, Final Office Action dated Oct. 8, 2015", 7 pgs.

"U.S. Appl. No. 13/445,179, Non Final Office Action dated Mar. 13, 2015", 8 pgs.

"U.S. Appl. No. 13/445,179, Non Final Office Action dated Sep. 19, 2013", 6 pgs.

"U.S. Appl. No. 13/445,179, Non Final Office Action dated Dec. 28, 2012", 5 pgs.

"U.S. Appl. No. 13/445,179, Notice of Allowance dated Jan. 12, 2016", 7 pgs.

"U.S. Appl. No. 13/445,179, Notice of Allowance dated Apr. 26, 2016", 7 pgs.

"U.S. Appl. No. 13/445,179, Response filed Mar. 1, 2013 to Non Final Office Action dated Dec. 28, 2012", 8 pgs.

"U.S. Appl. No. 13/445,179, Response filed Jun. 23, 2015 to Non Final Office Action dated Mar. 13, 2015", 15 pgs.

"U.S. Appl. No. 13/445,179, Response filed Jul. 8, 2014 to Final Office Action dated May 21, 2014", 4 pgs.

"U.S. Appl. No. 13/445,179, Response filed Sep. 2, 2013 to Final Office Action dated Jul. 10, 2013", 6 pgs.

"U.S. Appl. No. 13/445,179, Response filed Dec. 2, 2013 to Non Final Office Action dated Sep. 19, 2013", 8 pgs.

"U.S. Appl. No. 13/445,179, Response filed Dec. 14, 2015 to Final Office Action dated Oct. 8, 2015", 8 pgs.

"International Application Serial No. PCT/US2012/033526, International Preliminary Report on Patentability dated Oct. 24, 2013", 6 pgs.

"International Application Serial No. PCT/US2012/033526, International Search Report dated Jul. 5, 2012", 3 pgs.

"International Application Serial No. PCT/US2012/033526, Written Opinion dated Jul. 5, 2012", 4 pgs.

"Japanese Application Serial No. 2014-505337, Office Action dated Mar. 2, 2016", With English Translation, 7 pgs.

Bradley, Kerry, "Neurostimulation System and Method with Anatomy and Physiology Driven Programming", U.S. Appl. No. 61/390,112, filed Oct. 5, 2010.

Kothandaraman, Sridhar, et al., "System and Method for Defining Neurostimulation Lead Configurations", U.S. Appl. No. 61/333,673, filed May 11, 2010.

"Japanese Application Serial No. 2014-505337, Amendment filed Dec. 18, 2013".

"Japanese Application Serial No. 2014-505337, Response filed Sep. 2, 2016 to Office Action dated Mar. 2, 2016", (English Translation of Claims), 6 pgs.

USER INTERFACE WITH VIEW FINDER FOR LOCALIZING ANATOMICAL REGION

RELATED APPLICATION DATA

The present application is a continuation of U.S. application Ser. No. 13/445,179, filed Apr. 12, 2012, now issued as U.S. Pat. No. 9,433,795, which claims the benefit under 35 U.S.C. § 119 to U.S. provisional patent application Ser. No. 61/474,884, filed Apr. 13, 2011. The foregoing applications are hereby incorporated by reference into the present application in their entirety.

FIELD OF THE INVENTION

The present invention relates to medical systems, and more particularly, to a user interface for displaying anatomical regions of patients.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations Peripheral Nerve Stimulation (PNS) systems have demonstrated efficacy in the treatment of chronic pain syndromes and incontinence, and a number of additional applications are currently under investigation. Also, Functional Electrical Stimulation (FES) systems such as the Freehand system by NeuroControl (Cleveland, Ohio) have been applied to restore some functionality to paralyzed extremities in spinal cord injury patients.

These implantable neurostimulation systems typically include one or more electrode carrying neurostimulation leads, which are implanted at the desired stimulation site, and a neurostimulator (e.g., an implantable pulse generator (IPG)) implanted remotely from the stimulation site, but coupled either directly to the neurostimulation lead(s) or indirectly to the neurostimulation lead(s) via a lead extension. Thus, electrical pulses can be delivered from the neurostimulator to the neurostimulation leads to stimulate the tissue and provide the desired efficacious therapy to the patient. The neurostimulation system may further comprise a handheld patient programmer in the form of a remote control (RC) to remotely instruct the neurostimulator to generate electrical stimulation pulses in accordance with selected stimulation parameters. The RC may, itself, be programmed by a clinician, for example, by using a clinician's programmer (CP), which typically includes a general purpose computer, such as a laptop, with a programming software package installed thereon.

In the context of an SCS procedure, one or more neurostimulation leads are introduced through the patient's back into the epidural space, such that the electrodes carried by the leads are arranged in a desired pattern and spacing to create an electrode array. Multi-lead configurations have been increasingly used in electrical stimulation applications (e.g., neurostimulation, cardiac resynchronization therapy, etc.). In the neurostimulation application of SCS, the use of multiple leads increases the stimulation area and penetration depth (therefore coverage), as well as enables more combinations of anodic and cathodic electrodes for stimulation, such as transverse multipolar (bipolar, tripolar, or quadrapolar) stimulation, in addition to any longitudinal single lead configuration. After proper placement of the neurostimulation leads at the target area of the spinal cord, the leads are anchored in place at an exit site to prevent movement of the neurostimulation leads. To facilitate the location of the neurostimulator away from the exit point of the neurostimulation leads, lead extensions are sometimes used.

The neurostimulation leads, or the lead extensions, are then connected to the IPG, which can then be operated to generate electrical pulses that are delivered, through the electrodes, to the targeted tissue, and in particular, the dorsal column and dorsal root fibers within the spinal cord. The stimulation creates the sensation known as paresthesia, which can be characterized as an alternative sensation that replaces the pain signals sensed by the patient.

The efficacy of SCS is related to the ability to stimulate the spinal cord tissue corresponding to evoked paresthesia in the region of the body where the patient experiences pain. Thus, the working clinical paradigm is that achievement of an effective result from SCS depends on the neurostimulation lead or leads being placed in a location (both longitudinal and lateral) relative to the spinal tissue such that the electrical stimulation will induce paresthesia located in approximately the same place in the patient's body as the pain (i.e., the target of treatment). If a lead is not correctly positioned, it is possible that the patient will receive little or no benefit from an implanted SCS system. Thus, correct lead placement can mean the difference between effective and ineffective pain therapy.

As such, the CP (described briefly above) may be used to instruct the neurostimulator to apply electrical stimulation to test placement of the leads and/or electrodes inter-operatively (i.e., in the context of an operating room (OR) mapping procedure), thereby assuring that the leads and/or electrodes are implanted in effective locations within the patient. The patient may provide verbal feedback regarding the presence of paresthesia over the pain area, and based on this feedback, the lead positions may be adjusted and re-anchored if necessary. Any incisions are then closed to fully implant the system.

Post-operatively (i.e., after the surgical procedure has been completed), a fitting procedure, which may be referred to as a navigation session, may be performed using the CP to program the RC, and if applicable the IPG, with a set of stimulation parameters that best addresses the painful site, thereby optimizing or re-optimizing the therapy. Thus, the navigation session may be used to pinpoint the stimulation region or areas correlating to the pain. Such programming ability is particularly advantageous after implantation should the leads gradually or unexpectedly move, which if uncorrected, would relocate the paresthesia away from the pain site.

Typical programmable neurostimulation systems require a means to locate and navigate to a targeted implant location. For example, in the context of SCS, the CP may display graphical representations of the neurostimulation leads in relation to the spinal column of the patient, as described in U.S. Provisional Patent Application Ser. No. 61/390,112, entitled Neurostimulation System and Method with Anatomy and Physiology Driven Programming," which is expressly incorporated herein by reference. Because it is desirable that the entire work area for an implant be displayed to medical personnel, current neurostimulation systems should display the entire spinal column, since neurostimulation leads can be implanted anywhere within the spinal column. However, because the size of a neurostimulation lead is much smaller than that of the spinal column, standard user interfaces are limited in that displaying the neurostimulation leads in the context of the entire spinal column may render any details of the neurostimulation leads and the immediately relevant region of the spinal column illegible.

There, thus, remains a need to provide a user interface capable of displaying an implant in the context of the entire work area while also displaying any details of the implant and the immediately surrounding portion of the work area in a legible manner.

SUMMARY OF THE INVENTION

In accordance with the present inventions, an external control device for use with a medical component (e.g., a neurostimulation lead) implanted within a patient is provided. The external control device comprises a user interface configured for receiving input from a user, displaying a first graphical representation of the medical component in the context of a global view of an anatomical region (e.g., a spinal column) of the patient, displaying a view finder (e.g., a box) spatially defining a portion of the global graphical representation of the anatomical region, and displaying a second graphical representation of the medical component in the context of a local graphical representation of the portion of the anatomical region portion spatially defined by the view finder.

The external control device further comprises control circuitry configured for, in response to the input from the user, modifying displayed view finder to spatially define a different portion of the global graphical representation of the anatomical region, such that the second graphical representation of the medical component is displayed in the context of a local graphical representation of the different portion of the anatomical region. The control circuitry may be configured for, in response to the input from the user, modifying the displayed view finder by changing a position of the displayed view finder relative to the global graphical representation. In one embodiment, the control circuitry is configured for, in response to the input from the user, limiting the change in the position of the displayed view finder in one dimension. In another embodiment, the control circuitry is configured for, in response to the input from the user, changing the position of the displayed view finder in two dimensions. The control circuitry may alternatively or additionally be configured for, in response to the input from the user, modifying the displayed view finder by changing a size of the displayed view finder.

In one embodiment, the user interface comprises a control element configured for being manipulated by the user, and the control circuitry is configured for modifying the displayed view finder to spatially define the different portion of the global graphical representation of the anatomical region in response to the user manipulation of the control element, e.g., a graphical control element. The graphical control element may be disposed on the view finder. Or, the graphical control element may be separate from the view finder. For example, the graphical control element may comprise a graphical slider bar. The user input may comprise manipulating a pointing device, in which case, the graphical control element may be configured for being manipulated via the pointing device.

In an optional embodiment, the control circuitry is further configured for, in response to additional input from the user, defining a location of the graphical representation of the medical device relative to at least one of the global graphical representation of the anatomical region and the local graphical representation of the portion of the anatomical region. In another optional embodiment, the control circuitry is further configured for, in response to additional input from the user, programming the medical component.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
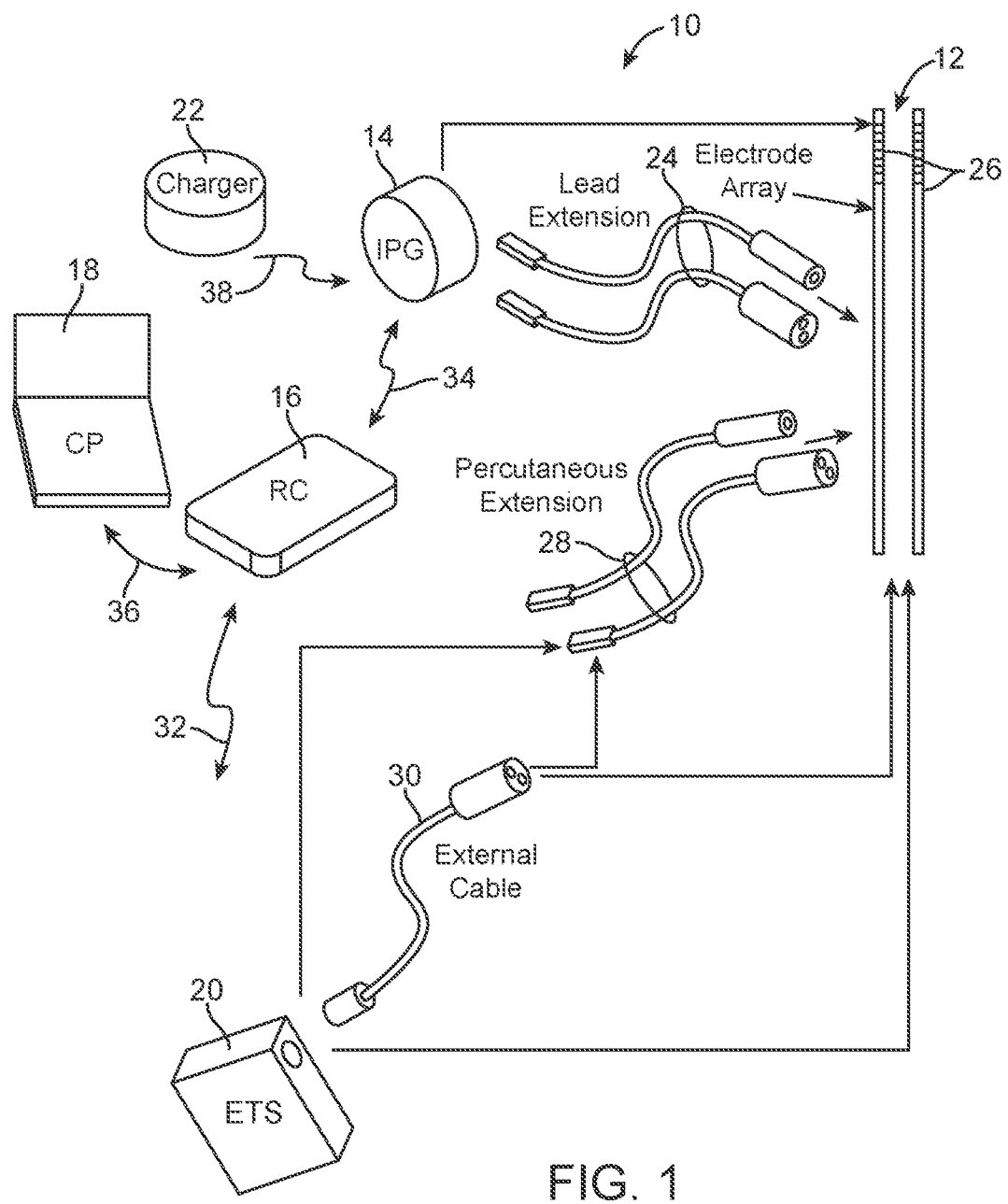
FIG. 1 is perspective view of one embodiment of a SCS system arranged in accordance with the present inventions.

Turning first to FIG. 1, an exemplary SCS system 10 generally includes a plurality (in this case, two) of implantable neurostimulation leads 12, an implantable pulse generator (IPG) 14, an external remote controller RC 16, a clinician's programmer (CP) 18, an external trial stimulator (ETS) 20, and an external charger 22.

The IPG 14 is physically connected via one or more percutaneous lead extensions 24 to the neurostimulation leads 12, which carry a plurality of electrodes 26 arranged in an array. In the illustrated embodiment, the neurostimulation leads 12 are percutaneous leads, and to this end, the electrodes 26 are arranged in-line along the neurostimulation leads 12. The number of neurostimulation leads 12 illustrated is two, although any suitable number of neurostimulation leads 12 can be provided, including only one. Alternatively, a surgical paddle lead in can be used in place of one or more of the percutaneous leads. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and neurostimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
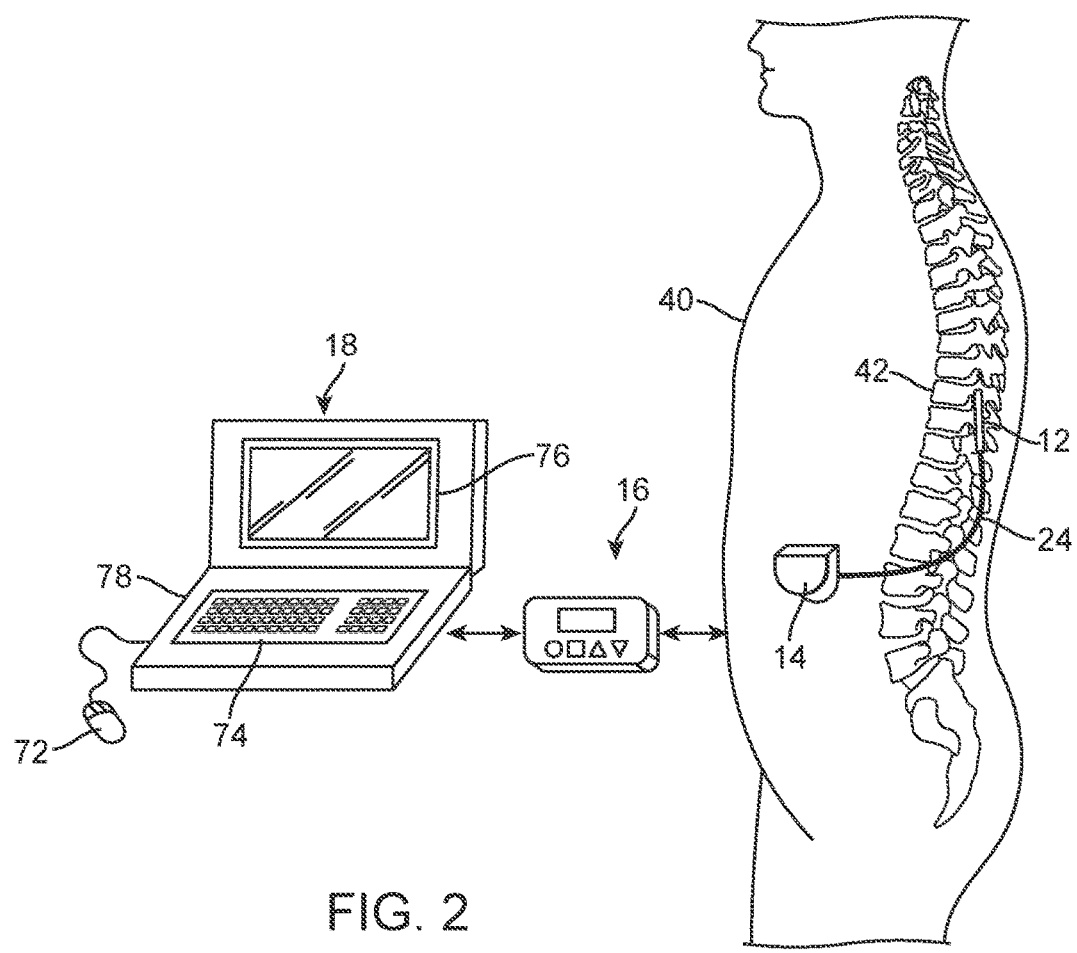
FIG. 2 is a plan view of the SCS system of FIG. 1 in use with a patient.

As shown in FIG. 2, the neurostimulation leads 12 are implanted within the spinal column 42 of a patient 40. The preferred placement of the neurostimulation leads 12 is adjacent, i.e., resting upon, the spinal cord area to be stimulated. Due to the lack of space near the location where the neurostimulation leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the neurostimulation leads 12. As there shown, the CP 18 communicates with the IPG 14 via the RC 16.

Figure 3:
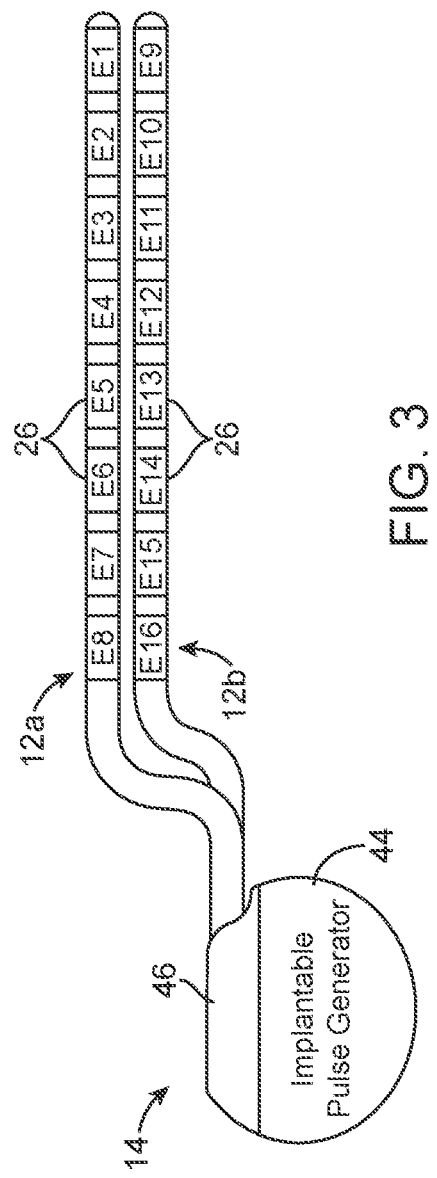
FIG. 3 is a side view of an implantable pulse generator and a pair of stimulation leads that can be used in the SCS system of FIG. 1.

Referring now to FIG. 3, the external features of the neurostimulation leads 12 and the IPG 14 will be briefly described. One of the neurostimulation leads 12a has eight electrodes 26 (labeled E1-E8), and the other stimulation lead 12b has eight electrodes 26 (labeled E9-E16). The actual number and shape of leads and electrodes will, of course, vary according to the intended application. The IPG 14 comprises an outer case 40 for housing the electronic and other components (described in further detail below), and a connector 42 to which the proximal ends of the neurostimulation leads 12 mates in a manner that electrically couples the electrodes 26 to the electronics within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

The IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

In the illustrated embodiment, IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

It should be noted that rather than an IPG, the SCS system 10 may alternatively utilize an implantable receiver-stimulator (not shown) connected to the neurostimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 4:
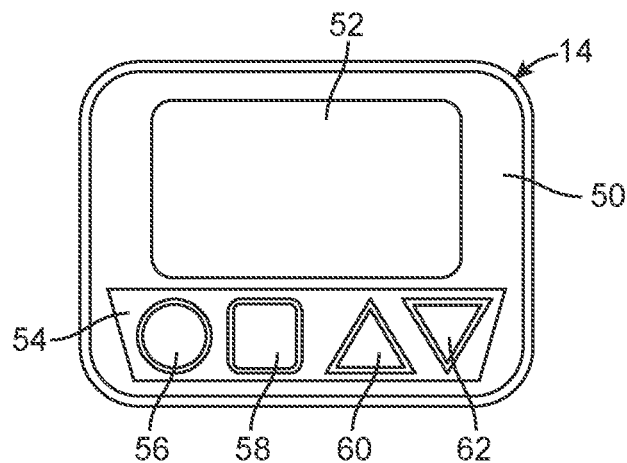
FIG. 4 is a plan view of a remote control that can be used in the SCS system of FIG. 1.

Referring now to FIG. 4, one exemplary embodiment of an RC 16 will now be described. As previously discussed, the RC 16 is capable of communicating with the IPG 14, CP 18, or ETS 20. The RC 16 comprises a casing 50, which houses internal componentry (including a printed circuit board (PCB)), and a lighted display screen 52 and button pad 54 carried by the exterior of the casing 50. In the illustrated embodiment, the display screen 52 is a lighted flat panel display screen, and the button pad 54 comprises a membrane switch with metal domes positioned over a flex circuit, and a keypad connector connected directly to a PCB. In an optional embodiment, the display screen 52 has touchscreen capabilities. The button pad 54 includes a multitude of buttons 56, 58, 60, and 62, which allow the IPG 14 to be turned ON and OFF, provide for the adjustment or setting of stimulation parameters within the IPG 14, and provide for selection between screens.

In the illustrated embodiment, the button 56 serves as an ON/OFF button that can be actuated to turn the IPG 14 ON and OFF. The button 58 serves as a select button that allows the RC 16 to switch between screen displays and/or parameters. The buttons 60 and 62 serve as up/down buttons that can be actuated to increment or decrement any of stimulation parameters of the pulse generated by the IPG 14, including pulse amplitude, pulse width, and pulse rate. For example, the selection button 58 can be actuated to place the RC 16 in a "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 5:
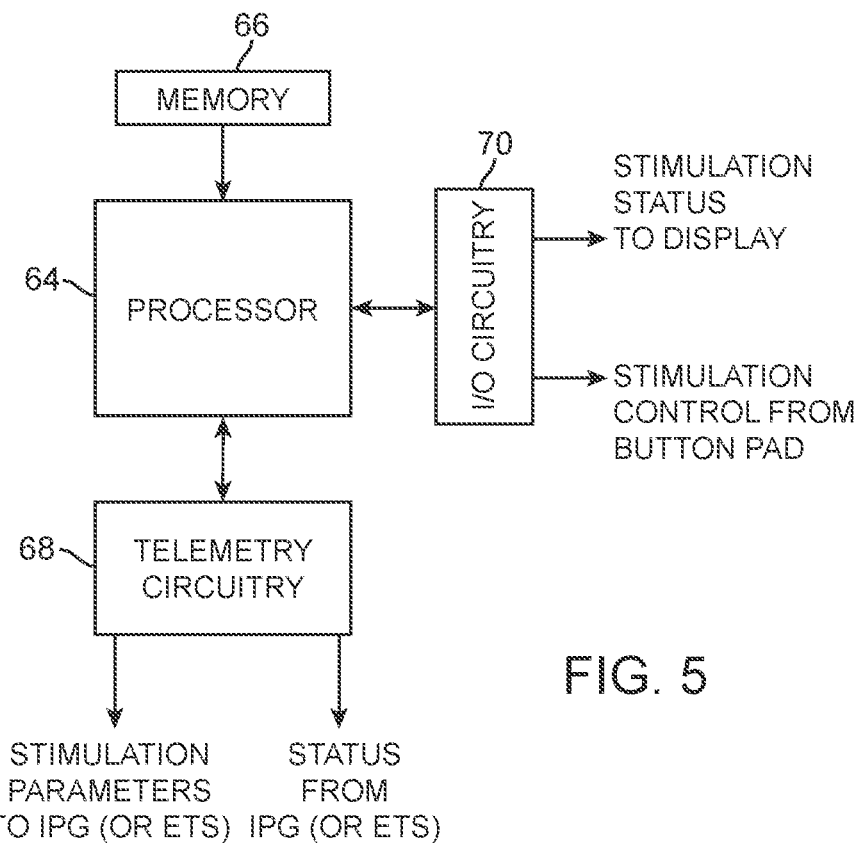
FIG. 5 is a block diagram of the internal componentry of the remote control of FIG. 4.

Referring to FIG. 5, the internal components of an exemplary RC 16 will now be described. The RC 16 generally includes a processor 64 (e.g., a microcontroller), memory 66 that stores an operating program for execution by the processor 64, as well as stimulation parameter sets in a navigation table (described below), input/output circuitry, and in particular, telemetry circuitry 68 for outputting stimulation parameters to the IPG 14 and receiving status information from the IPG 14, and input/output circuitry 70 for receiving stimulation control signals from the button pad 54 and transmitting status information to the display screen 52 (shown in FIG. 4). As well as controlling other functions of the RC 16, which will not be described herein for purposes of brevity, the processor 64 generates new stimulation parameter sets in response to the user operation of the button pad 54. These new stimulation parameter sets would then be transmitted to the IPG 14 via the telemetry circuitry 68. Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the user (e.g., the physician or clinician) to readily determine the desired stimulation parameters to be programmed into the IPG 14, as well as the RC 16. Thus, modification of the stimulation parameters in the programmable memory of the IPG 14 after implantation is performed by a user using the CP 18, which can directly communicate with the IPG 14 or indirectly communicate with the IPG 14 via the RC 16. That is, the CP 18 can be used by the user to modify operating parameters of the electrode array 26 near the spinal cord.

As shown in FIG. 2, the overall appearance of the CP 18 is that of a laptop personal computer (PC), and in fact, may be implemented using a PC that has been appropriately configured to include a directional-programming device and programmed to perform the functions described herein. Alternatively, the CP 18 may take the form of a mini-computer, personal digital assistant (PDA), etc., or even a remote control (RC) with expanded functionality. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient feedback and for subsequently programming the IPG 14 with the optimum stimulation parameters.

To allow the user to perform these functions, the CP 18 includes a mouse 72, a keyboard 74, and a programming display screen 76 housed in a case 78. It is to be understood that in addition to, or in lieu of, the mouse 72, other directional programming devices may be used, such as a trackball, touchpad, joystick, or directional keys included as part of the keys associated with the keyboard 74.

In the illustrated embodiment described below, the display screen 76 takes the form of a conventional screen, in which case, a virtual pointing device, such as a cursor controlled by a mouse, joy stick, trackball, etc, can be used to manipulate graphical objects on the display screen 76. In alternative embodiments, the display screen 76 takes the form of a digitizer touch screen, which may either passive or active. If passive, the display screen 76 includes detection circuitry that recognizes pressure or a change in an electrical current when a passive device, such as a finger or non-electronic stylus, contacts the screen. If active, the display screen 76 includes detection circuitry that recognizes a signal transmitted by an electronic pen or stylus. In either case, detection circuitry is capable of detecting when a physical pointing device (e.g., a finger, a non-electronic stylus, or an electronic stylus) is in close proximity to the screen, whether it be making physical contact between the pointing device and the screen or bringing the pointing device in proximity to the screen within a predetermined distance, as well as detecting the location of the screen in which the physical pointing device is in close proximity. When the pointing device touches or otherwise is in close proximity to the screen, the graphical object on the screen adjacent to the touch point is "locked" for manipulation, and when the pointing device is moved away from the screen the previously locked object is unlocked.

Figure 6:
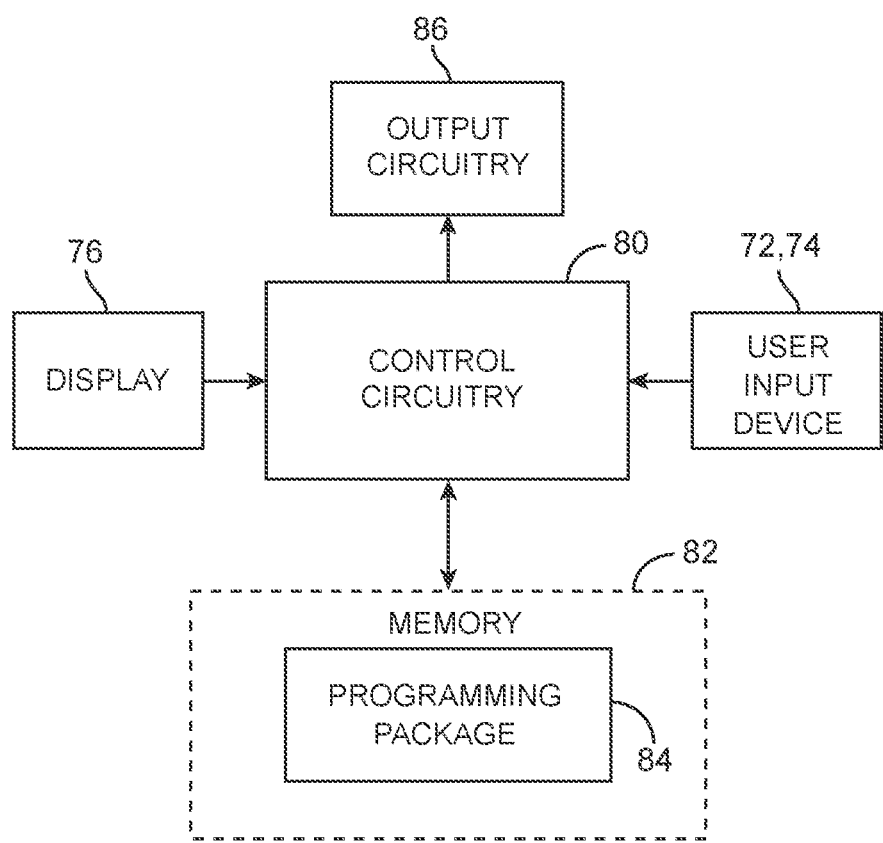
FIG. 6 is a block diagram of the components of a clinician programmer that can be used in the SCS system of FIG. 1.

As shown in FIG. 6, the CP 18 generally includes control circuitry 80 (e.g., a central processor unit (CPU)) and memory 82 that stores a stimulation programming package 84, which can be executed by the control circuitry 80 to allow the user to program the IPG 14, and RC 16. The CP 18 further includes output circuitry 86 (e.g., via the telemetry circuitry of the RC 16) for downloading stimulation parameters to the IPG 14 and RC 16 and for uploading stimulation parameters already stored in the memory 66 of the RC 16, via the telemetry circuitry 68 of the RC 16.

Execution of the programming package 84 by the control circuitry 80 provides a multitude of display screens (not shown) that can be navigated through via use of the mouse 72. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the neurostimulation leads 12, and select and program the IPG 14 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neurostimulation Electrodes," which are expressly incorporated herein by reference.

Most pertinent to the present inventions, programming of the IPG 14 can be performed based on a user-defined lead configuration corresponding to the actual configuration in which the neurostimulation leads 12 are physically implanted within the patient. This lead configuration is graphically displayed in the context of an anatomical region, and in this case, the spinal column of the patient. Preferably, the lead configuration is defined by the user to correspond with the actual configuration of the neurostimulation leads 12 within the patient, which can be obtained using suitable means, such as viewing a fluoroscopic image of the neurostimulation leads 12 and surrounding tissue of the patient, or using electrical means, such as transmitting electrical signals between the electrodes carried by the respective leads and measuring electrical parameters in response to the electrical signals, such as, e.g., any one or more of the manners disclosed in U.S. Pat. No. 6,993,384, entitled "Apparatus and Method for Determining the Relative Position and Orientation of Neurostimulation Leads," U.S. patent application Ser. No. 12/550,136, entitled "Method and Apparatus for Determining Relative Positioning Between Neurostimulation Leads," and U.S. patent application Ser. No. 12/623,976, entitled "Method and Apparatus for Determining Relative Positioning Between Neurostimulation Leads," which are expressly incorporated herein by reference.

Significantly, graphical representations of the neurostimulation leads 12 are displayed in the context of a composite graphical representation of the spinal column of the patient, comprising a global graphical representation of the spinal column and a local graphical representation of a portion of the spinal column. A view finder is displayed over a portion of the global graphical spinal column representation, such that the portion of the local graphical spinal column representation corresponds to the portion of the global graphical spinal column representation over which the view finder is displayed. The displayed view finder may be modified (e.g., by changing a position and/or size) to define a different portion of the global graphical spinal column representation, and the local graphical spinal column representation automatically updated to reflect the portion of the global graphical spinal column representation currently defined by the view finder. In this manner, the entirety of the spinal column work area may be quickly established and easily navigated using the global graphical representation, while allowing instant assessment of the location and programming status of the neurostimulation leads 12 using the local graphical representation.

Figure 7:
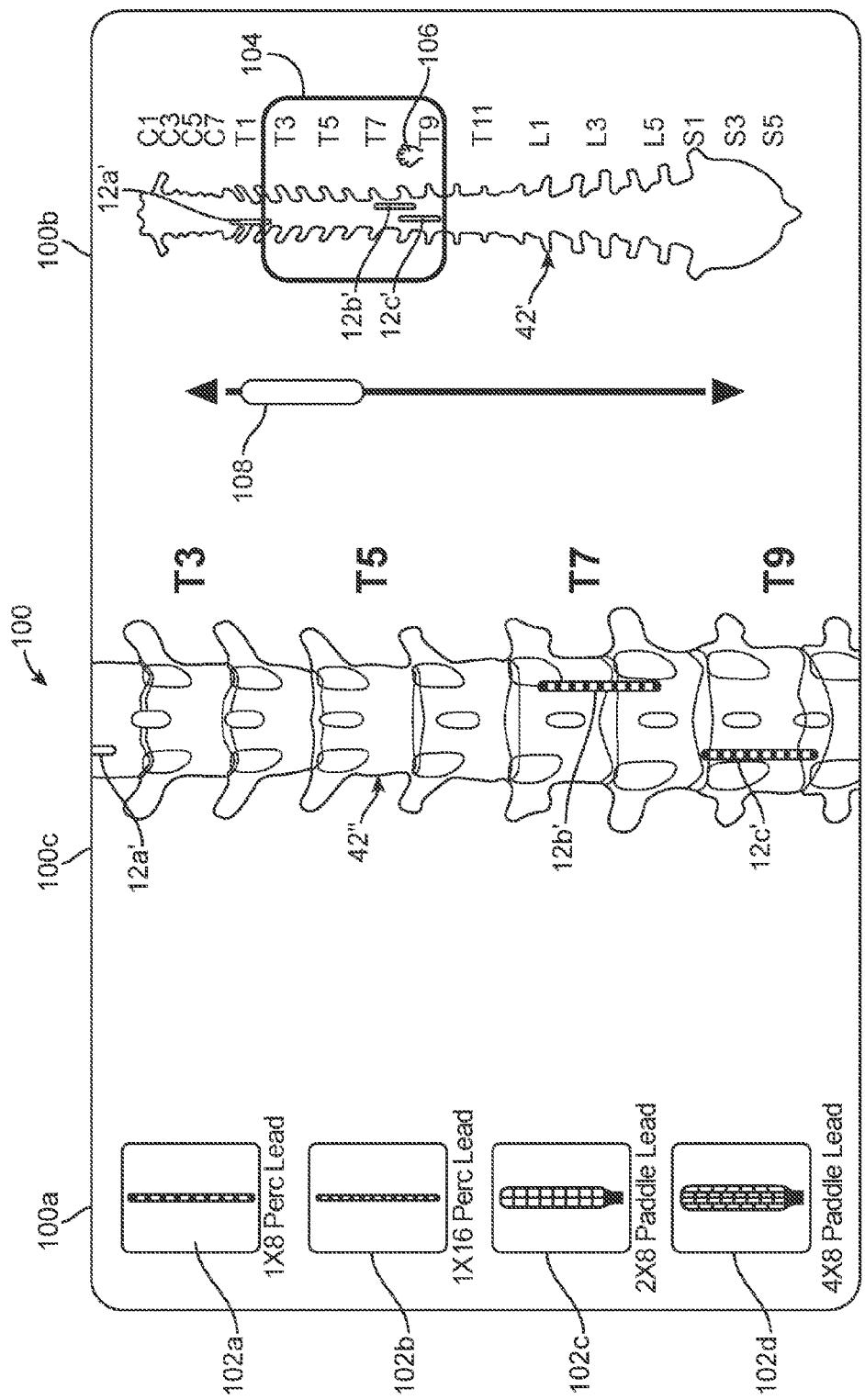
FIG. 7 is an illustration of a lead configuration screen that can be displayed by the clinician programmer of FIG. 6, wherein a graphical lead configuration is displayed over a composite graphical representation of a spinal column.

As one example, and with reference to FIG. 7, a lead configuration screen 100 illustrating a graphical representation of an adjustable lead configuration (in this case, consisting of three graphical lead representations 12') can be manipulated by the user to define the lead configuration that best matches the actual configuration of the neurostimulation leads 12. In the illustrated embodiment, the lead configuration screen 100 is segmented into a lead type selection section 100a displaying a plurality of lead generation icons 102a-102d, a global view section 100b displaying a global graphical representation of the spinal column 42', and a local view section 100c displaying a local graphical representation of the spinal column 42'.

In this embodiment, the graphical lead representations 12' are displayed in a staggered arrangement that presumably matches the side-by-side arrangement of the actual leads 12 implanted in the patient. The graphical lead representations 12' are illustrated as being superimposed over a composite graphical representation of spinal column 42 at locations matching the location of the spinal column 42 at which the actual leads 12 are implanted. The composite graphical representation of the spinal column 42 consists of the global graphical spinal column representation 42' and the local graphical spinal column representation 42".

In order to define the lead configuration, objects can be dragged and dropped from a selected one of a plurality of lead generation icons 102a-d to generate the graphical lead representations 12'. As example, the lead generation icons include 1×8 percutaneous lead generation icon 102a, a 1×16 percutaneous lead 102b, a 2×8 paddle lead 102c, and a 4×8 paddle lead 102d. The location of the graphical lead representations 12 relative to the global and local graphical spinal columns 42', 42", as well as the longitudinal distance and/or lateral distance between the graphical lead representations 12', can be defined in this manner. In the illustrated embodiment, objects are dragged and dropped from the 1×8 percutaneous lead generation icon 104a to create a lead configuration consisting of three virtual 1×8 percutaneous leads 12a', 12b, 12c'. The control circuitry 80 of the CP 18 allows the user to graphically create new lead configurations from the initial lead configuration by allowing the user to select one of the graphical lead representations 12' (e.g., by coupling to one of the graphical lead representations 12'), dragging the selected graphical lead representation 12' (e.g., by displacing the selected graphical lead representation 12' relative to the other graphical lead representation 12'), and dropping the displaced graphical lead representation 12' (e.g., by decoupling from the displaced graphical lead representation 12'). The object can either be dropped into the global view section 100b to define a graphical lead representation 12 relative to the global graphical spinal column 42' (in which case, the local view section 100c will be automatically updated with the graphical lead representation 12') or dropped into the local view section 100c to define a graphical lead representation 12 relative to the local graphical spinal column representation 42" (in which case, the global view section 100b will be automatically updated with the graphical lead representation 12').

The manner in which a graphical lead representation 12' is selected, dragged, and dropped will depend on the nature of the user interface. For example, if the display screen 76 is conventional, a virtual pointing device (e.g., cursor controlled by the mouse 72, joy stick, trackball, etc.) can be used to select, drag, and drop the graphical lead representations 12' into the global or local view sections 100b, 100c. If the display screen 76 is a digitizer screen, a physical pointing device (e.g., a stylus or finger) can be used to select, drag, and drop the graphical lead representations 12' into the global or local view sections 100b, 100c. Further details discussing the generation of lead configurations using a drag and drop technique are set forth in U.S. Provisional Patent Application Ser. No. 61/333,673, entitled "System and Method for Defining Neurostimulation Lead Configurations," which is expressly incorporated herein by reference.

As briefly discussed above, a view finder 104 is displayed over a portion of the global graphical spinal column representation 42'. In the illustrated embodiment, the view finder 104 takes the form of a box outline. Alternatively, the view finder 104 may take the form of other shapes, such as a circle outline. In the case illustrated in FIG. 7, the portion of the global graphical spinal column representation 42' over which the view finder 104 is displayed consists of the T7-T10 vertebral segments, and thus, the displayed local graphical spinal column representation 42" consists of the T7-T10 vertebral segments (including the entire graphical lead representations 12b and 12c).

The displayed view finder 104 may be displaced (and in this case, scrolled longitudinally along the global graphical spinal column representation 42') to another different portion of the global graphical spinal column representation 42', such that at least one of the graphical lead representations 12' is displayed in the local graphical representation of the other portion of the spinal column 42". Thus, as the view finder 104 is scrolled along the global graphical spinal column representation 42', the local graphical spinal column representation 42" will automatically update to reflect the portion of the global graphical spinal column representation 42" spatially defined by the view finder 104.

Figure 8:
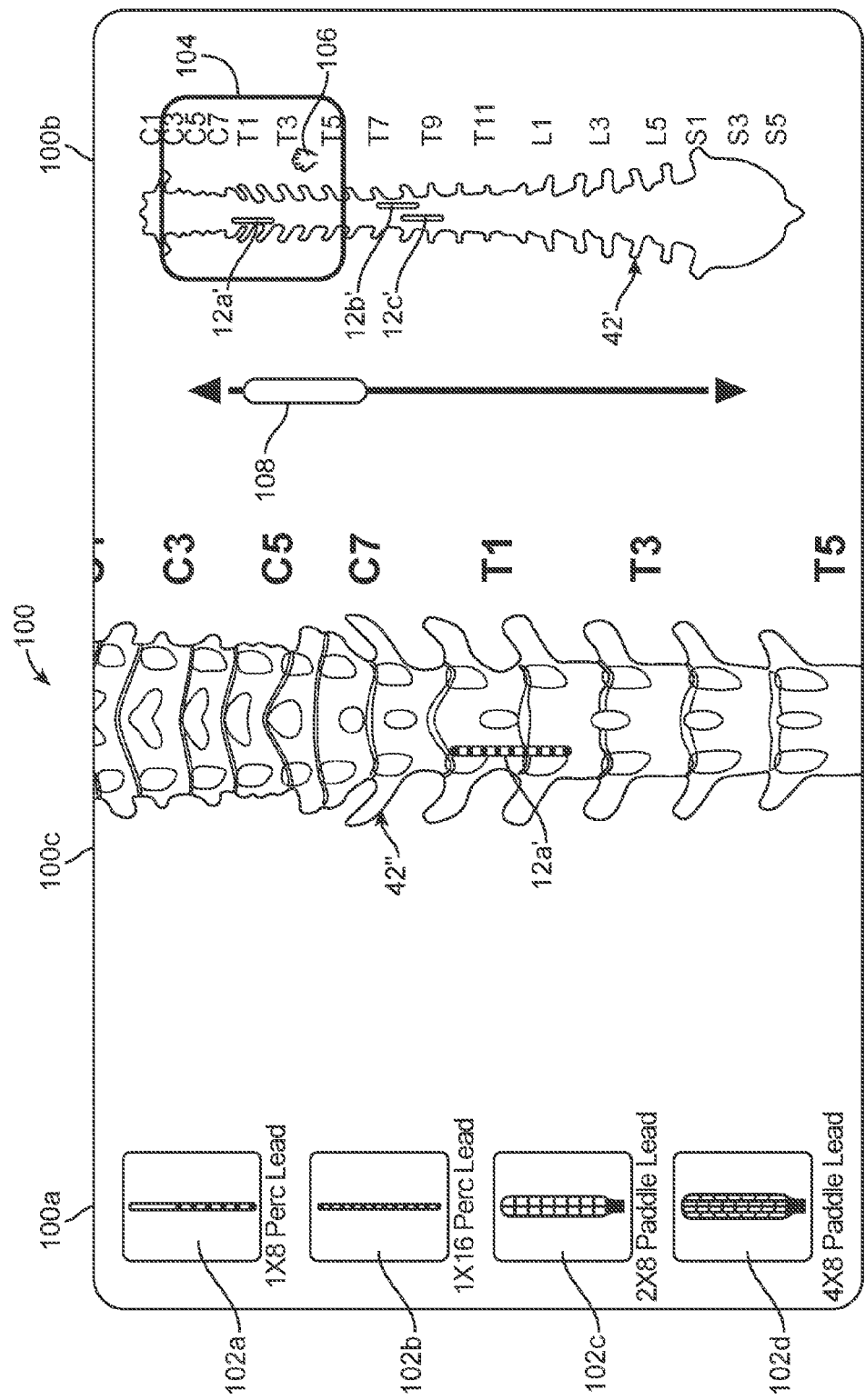
FIG. 8 is an illustration of the lead configuration screen of FIG. 7, wherein a view finder is displaced along the spinal column.

For example, as illustrated in FIG. 8, the different portion of the global graphical spinal column representation 42' over which the view finder 104 is displayed consists of the T1-T5 vertebral segments (including graphical lead representation 12a). In the illustrated embodiment, displacement of the view finder 104 is limited to one axis along the spinal column. In an optional embodiment, the view finder 104 may be displaced in the lateral direction (left and right), in addition to the longitudinal direction (up and down), thereby allowing the view finder 104 to be displaced in two dimensions.

The lead configuration screen 100 includes different control elements for displacing the view finder 104. For example, the view finder 104 may, itself, serve as a graphical control element. If the display screen 76 is conventional, the user may click on the view finder 104 using a virtual pointing device in the form of a graphical cursor 106 (shown as a hand) via a mouse 72 or other pointing device, and drag the view finder 104 to a different portion of the global graphical spinal column representation 42". If the display screen 76 is a digitizer screen, the user may place a physical pointing device adjacent the view finder 104 and draft the view finder 104 to a different portion of the global graphical spinal column representation 42". In the illustrated embodiment, the outline of the view finder 104 or any graphical space contained in the outline may be manipulated by the pointing device to displace the view finder 104.

Alternatively, the graphical control element may be completely separate from the view finder 104. For example, the graphical control element can take the form of a graphical slider bar 108, which in the exemplary lead configuration screen 100, is adjacent the local graphical spinal column representation 42'. The graphical slider bar 108 can be moved up or down using, e.g., a pointing device (not shown), to thereby scroll the view finder 104 longitudinally along the global graphical spinal column representation 42". As the view finder 104 is scrolled along the global graphical spinal column representation 42", the local graphical spinal column representation 42" will automatically update to reflect the portion of the global graphical spinal column representation 42" within the view finder 104.

In other embodiments, the control element may be simply be distributed on the local graphical spinal column representation 42' and surrounding area on the display screen 100. That is, any area in the local view section 100c can be manipulated (e.g., clicked or touched) using, e.g., a pointing device (not shown), to thereby scroll the view finder 104 longitudinally along the global graphical spinal column representation 42". Again, as the view finder 104 is scrolled along the global graphical spinal column representation 42", the local graphical spinal column representation 42" will automatically update to reflect the portion of the global graphical spinal column representation 42" within the view finder 104.

In an optional embodiment, the individual vertebral segments (or the vertebral segment labels) of the global graphical spinal column representation 42" the individual lead representations 12' displayed on the global view section 100b may serve as graphical control elements. For example, any of the vertebral segments or lead representations can be clicked or otherwise touched, such that the view finder 104 is automatically centered on the vertebral segment or lead representation that is clicked or touched. For example, if any portion of the vertebral segment T7 is clicked or touched, the view finder 104 may be automatically centered on the vertebral segment T7, such that the center of the vertebral segment T7 coincides with the center of the view finder 104 in the global view section 100*b*, and therefore, is centered in the local view section 100*c*. Similarly, if any portion of the graphical lead representation 12*b* is clicked or touched, the view finder 104 may be automatically centered on the graphical lead representation 12*b*, such that the center of the graphical lead representation 12*b* coincides with the center of the view finder 104 in the global view section 100*b*, and therefore, is centered in the local view section 100*c*. In still another optional embodiment, if the control element may be distributed on the graphical view section 100*b*, such that any point that is clicked or touched on the graphical view section 100*b* will prompt the view finder 104 to be centered on that point.

Figure 9:
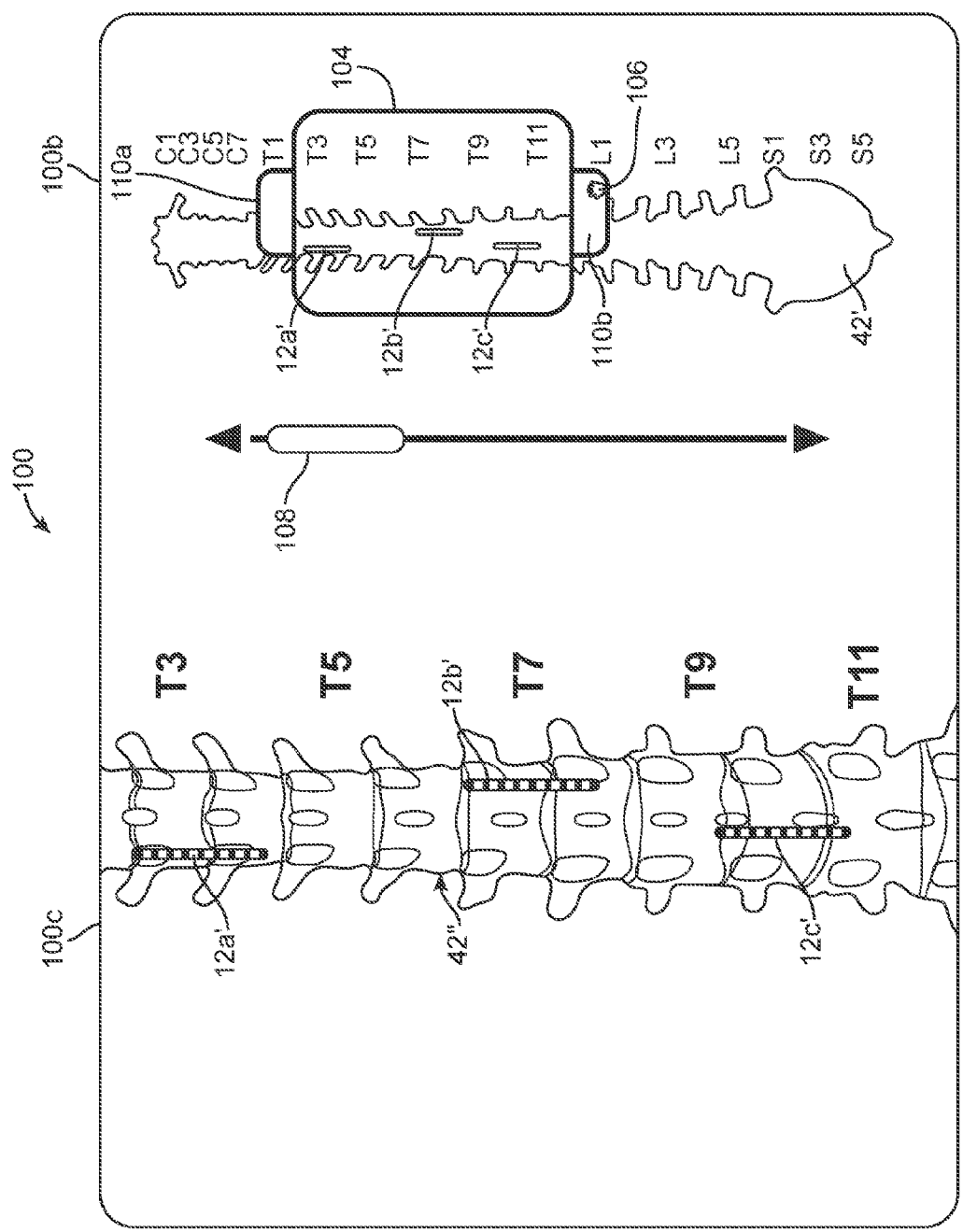
FIG. 9 is an illustration of the lead configuration screen of FIG. 7, wherein the view finder is expanded.
Figure 10:
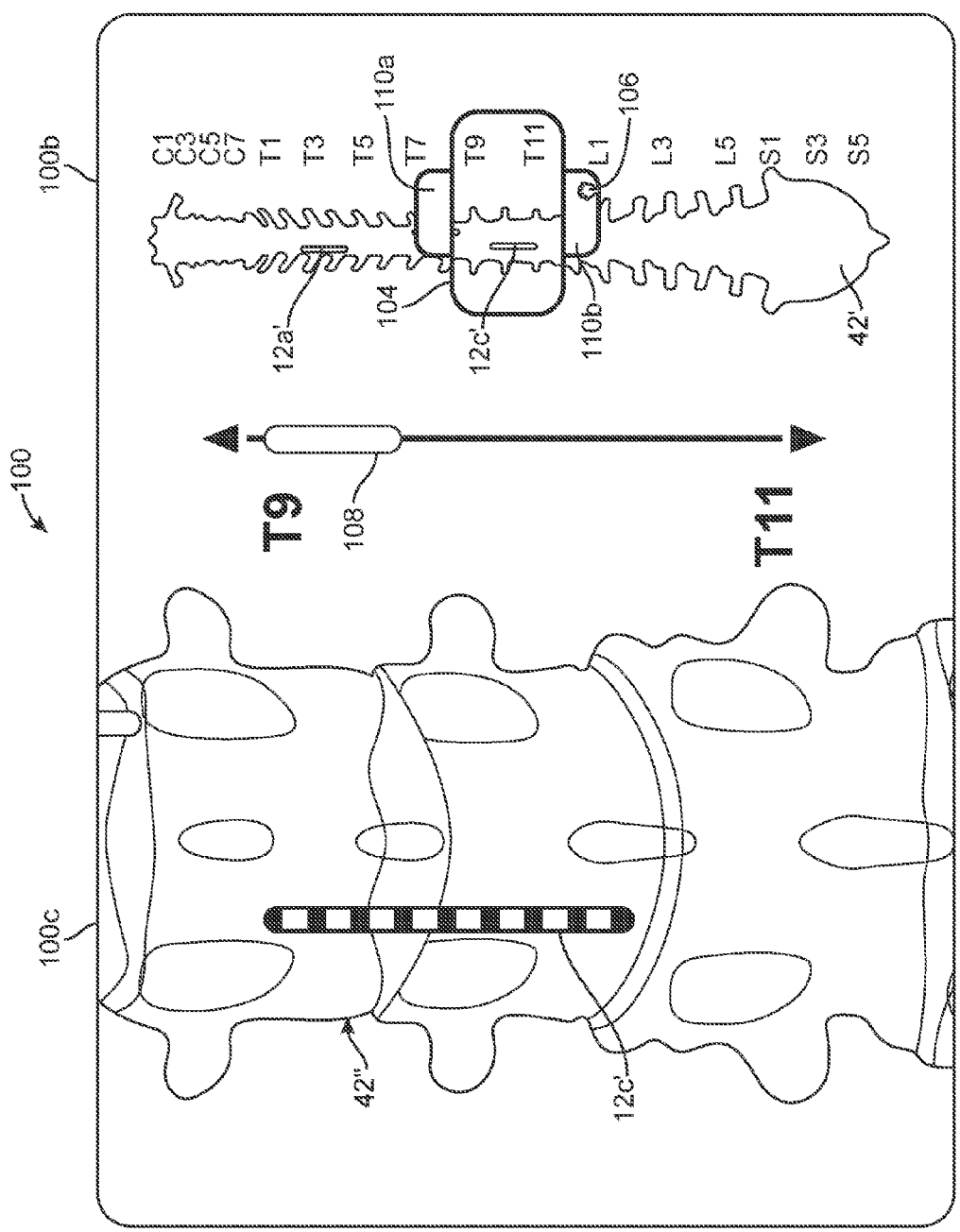
FIG. 10 is an illustration of the lead configuration screen of FIG. 7, wherein the view finder is contracted.

In addition to being displaced, the size of the displayed view finder 104 may optionally be changed; for example, expanded or contracted, such that the size of the local graphical spinal column representation 42" is correspondingly changed. The lead configuration screen 100 may include different control elements for displacing the view finder 104. For example, as shown in FIGS. 9 and 10, control elements may take the form of upper and lower handles 110*a*, 110*b* respectively extending from the top and bottom borders of the view finder 104. Either of the handles 110 can be dragged using a pointing device (not shown) to expand or contact the view finder 104 in the upward or downward direction. For example, the upper handle 110*a* may be dragged upward to correspondingly expand the view finder 104 in the upward direction, as shown in FIG. 9, or the upper handle 110*a* may be dragged downward to correspondingly contract the view finder 104 in the downward direction, as shown in FIG. 10. It can be appreciated that the lower handle 110*b* may be also dragged downward to correspondingly expand the view finder 104 in the downward direction, or the lower handle 110*b* may also be dragged upward to corresponding contract the view finder 104 in the upward direction. Optionally, left and right handles (not shown) can respectively extend from the left and right borders of the view finder 104. In this case, these handles may be dragged leftward or rightward to expand or contract the view finder 104 in the left or right directions.

As the view finder 100 is expanded or contracted, the local graphical spinal column representation 42" will automatically update to reflect the expanded or contracted portion of the global graphical spinal column representation 42" within the view finder 104. In the case illustrated in FIG. 9, the portion of the global graphical spinal column representation 42' over which the view finder 104 is displayed is expanded to consist of the T2-T11 vertebral segments, and thus, the displayed local graphical spinal column representation 42" is expanded to consist of the T2-T11 vertebral segments (including the entirety of all of the graphical lead representations 12). In the case illustrated in FIG. 10, the portion of the global graphical spinal column representation 42' over which the view finder 104 is displayed is contracted to consist of the T9-T11 vertebral segments, and thus, the displayed local graphical spinal column representation 42" is contracted to consist of the T9-T11 vertebral segments (including only the graphical lead representation 12*c*).

In alternative embodiments, the borders of the view finder 104, themselves, can be used as control elements that can be dragged to correspondingly expand or contract the view finder 104. In this case, the borders of the view finder 104 cannot be used to displace the view finder 104 in the manner discussed above with respect to FIGS. 7 and 8. Instead, the pointing device may be placed adjacent the interior of the view finder 104 to displace it.

Once the lead configuration is established in the lead configuration screen 100, a different display screen can be accessed to program the neurostimulation leads 12 with the desired stimulation parameters, e.g., in the manner described in U.S. patent application Ser. No. 12/501,282, which has been previously incorporated herein by reference.

Although the foregoing technique has been described as being implemented in the CP 18, it should be noted that this technique may be alternatively or additionally implemented in the RC 16. Furthermore, although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An external control device for use with a medical component implanted within a patient, comprising:
   a user interface configured to display a view of a graphical representation of an anatomical region of the patient and a medical component in the context of the graphical representation of the anatomical region of the patient;
   the user interface further configured to receive a first user input to pan the view to display a different portion for the graphical representation and a second user input to change a size of the view; and
   control circuitry configured to, in response to the first user input, display the different portion for the graphical representation, the control circuitry further configured to, in response to the second user input, automatically change a size of the view.

2. The external control device of claim 1 wherein the second user input includes at least one handle corresponding to a first direction and configured to expand or contract the view in the first direction.

3. The external control device of claim 1 wherein the second user input includes a first handle corresponding to a first direction and configured to expand or contract the view in the first direction and a second handle corresponding to a second direction and configured to expand or contract the view in the second direction.

4. The external control device of claim 1 wherein the first user input includes a graphical slider bar.

5. The external control device of claim 1 wherein the medical component includes a neurostimulation lead, and the anatomical region includes a spinal column of the patient.

6. The external control device of claim 1 wherein the view is represented by a box.

7. The external control device of claim 1, wherein the control circuitry is further configured to, in response to additional input from the user, define a location of the graphical representation of the medical component relative to the graphical representation of the anatomical region.

8. The external control device of claim 1, wherein the control circuitry is further configured to, in response to additional input from the user, program the medical component.

9. An apparatus for use with a medical component implanted within a patient, the apparatus comprising:
 a user interface including a display;
 a processor; and
 a memory including instructions that, when performed by the processor, cause the apparatus to:
  present on the display a view of a graphical representation of an anatomical region of the patient and a medical component in the context of the graphical representation of the anatomical region of the patient;
  receive a first user input via the user interface to pan the view to present a different portion of the graphical representation and receive a second user input via the user interface to change a size of the view; and
  respond to the first user input by presenting the different portion for the graphical representation, and respond to the second user input by changing a size of the view.

10. The apparatus of claim 9 wherein the instruction includes instructions to present at least one handle corresponding to a first direction and used to expand or contract the view in the first direction.

11. The apparatus of claim 9 wherein the instruction includes instructions to present a first handle corresponding to a first direction and used to expand or contract the view in the first direction and a second handle corresponding to a second direction and used to expand or contract the view in the second direction.

12. The apparatus of claim 9 wherein the instructions present a graphical slider bar on the display used to pan the view.

13. The apparatus of claim 9 wherein the medical component includes a neurostimulation lead, and the anatomical region includes a spinal column of the patient.

14. The apparatus of claim 9 wherein the view is represented by a box.

15. The apparatus of claim 9, wherein the processor is further configured to, in response to additional input from the user, define a location of the graphical representation of the medical component relative to the graphical representation of the anatomical region.

16. The apparatus of claim 9, wherein the instructions include instructions to program the medical component in response to additional input from the user.

17. A method for providing a user interface in an external control device for use with a medical component implanted within a patient, the method comprising:
 displaying a view of a graphical representation of an anatomical region of the patient and the medical component in the context of the graphical representation of the anatomical region of the patient;
 receiving a first user input to pan the view to display a different portion for the graphical representation and a second user input to change a size of the view;
 displaying the different portion for the graphical representation in response to the first user input; and
 automatically change a size of the view in response to the second user input.

18. The method of claim 17 wherein the second user input includes at least one handle corresponding to a first direction and configured to expand or contract the view in the first direction.

19. The method of claim 17 wherein the second user input includes a first handle corresponding to a first direction and configured to expand or contract the view in the first direction and a second handle corresponding to a second direction and configured to expand or contract the view in the second direction.

20. The method of claim 17 further comprising programming the medical component in response to additional input from the user.

* * * * *